United States Patent
Sagiv et al.

(10) Patent No.: US 11,814,442 B2
(45) Date of Patent: Nov. 14, 2023

(54) IMMUNOGLOBULIN COMPOSITIONS AND PROCESS FOR OBTAINING THE SAME

(71) Applicant: KAMADA LTD., Rechovot (IL)

(72) Inventors: Yuval Sagiv, Gedera (IL); Shahar Nisemblat, Kfar Saba (IL)

(73) Assignee: KAMADA LTD., Rehovot (IL)

( * ) Notice: Subject to any disclaimer, the term of this patent is extended or adjusted under 35 U.S.C. 154(b) by 868 days.

(21) Appl. No.: 16/621,374

(22) PCT Filed: Jun. 12, 2018

(86) PCT No.: PCT/IL2018/050642
§ 371 (c)(1),
(2) Date: Dec. 11, 2019

(87) PCT Pub. No.: WO2018/229760
PCT Pub. Date: Dec. 20, 2018

(65) Prior Publication Data
US 2020/0157242 A1     May 21, 2020

Related U.S. Application Data

(60) Provisional application No. 62/518,005, filed on Jun. 12, 2017.

(51) Int. Cl.
*C07K 16/34* (2006.01)
*A61P 37/04* (2006.01)
*C07K 16/06* (2006.01)

(52) U.S. Cl.
CPC .............. *C07K 16/34* (2013.01); *A61P 37/04* (2018.01); *C07K 16/065* (2013.01)

(58) Field of Classification Search
None
See application file for complete search history.

(56) References Cited

U.S. PATENT DOCUMENTS

2013/0058961 A1   3/2013   Teschner et al.
2015/0210737 A1   7/2015   Vadde et al.

FOREIGN PATENT DOCUMENTS

AU   2015268579   12/2015
EP   3135687 A1    3/2017

OTHER PUBLICATIONS

Williams, S., et al., "Procoagulant Activity in Immunoglobulin Products," Journal of Thrombosis and Haemostasis, vol. 14, pp. 1-168 (Dec. 31, 2016)—Abstract.
Extended European Search Report dated Mar. 16, 2021 in corresponding European Patent Application No. 18818610.0.

*Primary Examiner* — Brian Gangle
(74) *Attorney, Agent, or Firm* — Wenderoth, Lind & Ponack, L.L.P.

(57) ABSTRACT

The invention provides human plasma-derived immunoglobulin compositions comprising low levels of thrombogenic agents and of IgG aggregates. The invention further provides methods for removing the active coagulation factors and IgG aggregates content of a plasma-derived immunoglobulin composition.

12 Claims, 4 Drawing Sheets

IMMUNOGLOBULIN COMPOSITIONS AND PROCESS FOR OBTAINING THE SAME

FIELD OF THE INVENTION

The present invention relates to human plasma-derived immunoglobulin compositions comprising low levels of thrombogenic agents and of IgG aggregates. The present invention further relates to methods for reducing the active coagulation factors content and IgG aggregates of a plasma-derived immunoglobulin composition.

BACKGROUND OF THE INVENTION

Immunoglobulins play an important role in the immune system of mammals. They are produced by B-lymphocytes, found in blood plasma, lymph and other body secretions. Immunoglobulins constitute approximately 20% of the plasma proteins in humans. The basic unit of immunoglobulins is a heterotetramer, containing two heavy chains and two light chains, linked by disulphide bonds. Each of these chains have a variable region at their N-terminus which form the antigen binding site, and constant regions, which are responsible for the effector functions of the immunoglobulins.

Immune globulin products from human plasma were first used to treat immune deficiency. Initially, intramuscular or subcutaneous administrations of Immunoglobulin isotype G (IgG) were the methods of choice.

Aggregates and denatured immunoglobulins, the amount of which can be increased by certain purification steps, especially are a potential risk for the patients because they have a high capacity to activate complement unspecifically, leading to severe side effects in patients receiving these denatured immunoglobulins. Unspecific complement activation refers to the initiation of the complement cascade in the absence of specific antibody-antigen complexes. Unspecific complement activation is strictly to be avoided since it may cause undesirable side effects such as hypotension, flushing, headache, fever, chills, nausea, vomiting, muscle pain, dyspnoea and tachycardia. Specific complement activation, on the other hand, is desirable and it occurs only after the immunoglobulins have bound to their specific antigens.

Dedicated coagulation factors, are integral components of both the contact activation and tissue factor pathways of the coagulation cascade. Upon a stimulus of the coagulation pathways, serine protease zymogens, which are inactive enzyme precursors, become activated proteases that catalyze the activation of the next protease zymogen, resulting in an activation cascade. This coagulation cascade culminates in the activation of Thrombin (Factor IIa) and Factor XIIIa, which function to convert Fibrinogen (Factor I) into Fibrin (Factor Ia) and cross-link fibrin to form a fibrin clot, respectively. The contact activation pathway, also known as the intrinsic coagulation pathway, begins with the activation of Factor XIIa (FXIIa) from Factor XII. The activated serine protease FXIIa cleaves Factor XI (FXI), converting the zymogen into Factor XIa (FXIa), an active serine protease which participates in the subsequent activation of Factor Xa (FXa).

Coagulation factor XI (FXI) is well known to be a protein involved in the initiation of blood coagulation and represents one part of the intrinsic pathway of the coagulation cascade. FXI is the precursor of activated FXI (FXIa), which is the active compound during coagulation. Therefore it is essential to remove FXIa from pharmaceutical preparations being applied to patients as said FXIa may unintentionally start coagulation leading to life endangering thrombotic events.

Due to rising concerns over the presence of serine protease, coagulation factors and serine protease zymogens in plasma-derived protein compositions, there remains a need in the art for methods for reducing the levels of these contaminants, and particularly FXI, FXIa, FXII, and FXIIa.

SUMMARY OF THE INVENTION

The present invention provides plasma-derived compositions with reduced levels of thrombogenic agents and high molecular weight forms of IgG. The present invention further provides an improved process for obtaining an IgG composition from human plasma.

The present invention is based in part on the unexpected discovery that gel filtration chromatography and euglobulin precipitation induce activation, aggregation and removal of coagulation factors. It was found according to the present invention that FXI and/or its active form FXIa can be effectively removed from an immunoglobulin containing solution by subjecting the immunoglobulin solution to gel filtration chromatography and euglobulin precipitation.

According to some embodiment of the present invention, the removal of coagulation factors by euglobulin precipitation and a week anion exchange chromatography is improved after their activations during gel filtration or any other activation pathway of the zymogens.

According to one aspect, the present invention provides an immunoglobulin composition isolated or purified from human plasma or fractions thereof, wherein said composition comprises (a) less or equal to 3% aggregates of equal or above 400 KDa, (b) NAPTT relative coagulation time (RCT) equal or above to 0.8, and (c) factor XI activity equal or below 8 mIU/ml (milli international units/milliliter).

According to certain embodiments, said immunoglobulin composition comprises less than 2.5% aggregates, less than 2% aggregates, less than 1.5% aggregates, or less than 0.8% aggregates. Each possibility represents a separate embodiment of the present invention.

According to certain embodiments, said immunoglobulin composition comprises factor XI activity equal or below 1 mIU/ml, preferably equal or below 0.5 mIU/ml, more preferably equal or below 0.36 mIU/ml. Each possibility represents a separate embodiment of the present invention.

According to certain embodiments, said RCT is equal or above to 0.9.

According to certain embodiments, the thrombogenic activity of the immunoglobulin composition as measured by Thrombin Generation Assay (TGA) is equal or below 3.19 mU/ml. According to certain embodiments, the thrombogenic activity of the immunoglobulin composition as measured by Thrombin Generation Assay (TGA) is equal or below 2.58 mU/mL.

According to certain embodiments, the immunoglobulin composition comprises purified polyclonal immunoglobulin G (IgG) fraction obtained from pooled human plasma from at least 25 donors.

According to certain embodiments, the immunoglobulin composition is suitable for intramuscular, subcutaneous, or intravenous administration to patients.

According to certain embodiments, the purified IgG fraction is equal or higher than 95% in relation to total proteins.

According to certain embodiments, the purified IgG fraction is equal or higher than 97% in relation to total proteins.

According to some embodiments, the immunoglobulin composition comprises at least 90%, preferably 95%, more preferably 98% IgG out of the total proteins. Each possibility represents a separate embodiment of the present invention. According to certain embodiments, said immunoglobulin composition is a pharmaceutical composition further comprising a pharmaceutically acceptable diluent or carrier.

According to some embodiments, the immunoglobulin composition comprises anti Rabies or anti-D IgG antibodies.

According to another aspect, the present invention provides a method for activating and removing a thrombogenic agent from an immunoglobulin containing solution, the method comprising the step of subjecting human plasma or fractions thereof to gel filtration column chromatography. According to some embodiments, the gel filtration column chromatography is a non-limiting example of activating the zymogens of the contact activation pathway.

According to some embodiments, the method further comprises Euglobulin precipitation step.

According to some embodiments, the Euglobulin precipitation is performed at a pH value within the range from about 4.6 to about 5.2. According to some embodiments, the immunoglobulin containing solution has a temperature in the range of about 17 to about 25° C. According to certain embodiments, the conductivity of the Euglobulin precipitation step is in the range of about 0.8 to about 1.2 mS/cm. According to certain embodiments, the conductivity of the Euglobulin precipitation step is in the range of about 0.9 to about 1.0 mS/cm.

According to some embodiments, the method further comprises an anion exchange column chromatography enrichment step. According to some embodiments the anion exchange column is a diethylaminoethyl (DEAE)-Sepharose resin column. According to some embodiments, the method further comprises at least one virus elimination treatment. According to some embodiments, the method further comprises at least two virus elimination treatments.

According to some embodiments, the thrombogenic agent is a coagulation factor selected from the group consisting of Factor II, Factor V, Factor VII, Factor VIII, von Willebrand factor, Factor IX, Factor X and Factor XI.

According to some embodiments, the present invention provides a method for activating and removing a thrombogenic agent and/or IgG aggregates from an immunoglobulin containing solution, the method comprising the steps of: (a) subjecting human plasma or fractions thereof to gel filtration column chromatography; (b) subjecting the protein containing fraction obtained by step (a) to euglobulin precipitation; and (c) loading the supernatants obtained by step (b) on an anion exchange column.

According to a further aspect, the present invention provides. a method of treating a subject suffering from an immunodeficiency, an inflammatory disease, an autoimmune disease, an antigen deficiency, or an acute infection, comprising administering to the subject an effective amount of an immunoglobulin composition.

Other objects, features and advantages of the present invention will become clear from the following description and drawings.

In process (IPC) samples from eight Anti-Rabies lots (columns) were used to determine coagulation activity by the Non-Activated Partial Thromboplastin Time (NAPTT) method. IPC samples were obtained from nine manufacturing steps throughout the process: post plasma pool (52204), filtered plasma pool (52201), post Gel Filtration (53202), post Euglobulins precipitation (53203), post DEAE column (53301), post Carboxy Methyl Sepharose (CM1) (56203), Load CM2 (54103), post CM2 (54104) and Drug substance—DS (54402/54906/55006). The coagulation time is compared with the coagulation time of a blank sample, used as control, and the coagulation activity is reported as the ratio between the two results (Relative Coagulation Time—RCT). A sample that coagulates within <80% of blank sample coagulation time (RCT<0.8) is considered thrombogenic.

Figure 2:
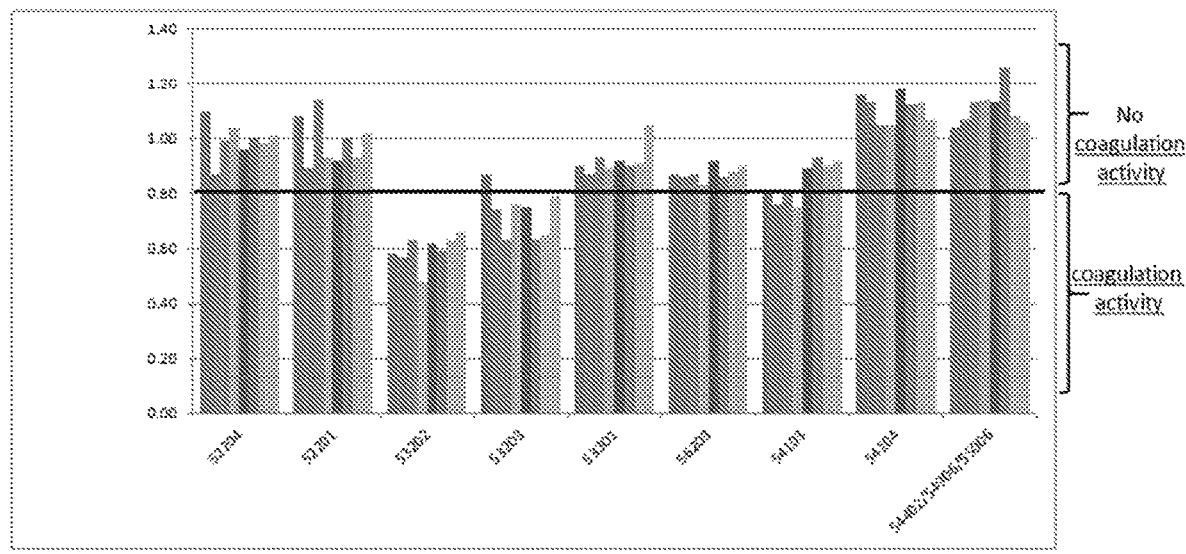

FIG. 2 depicts the Coagulation Activity of Anti-D IPC Samples.

Figure 1:
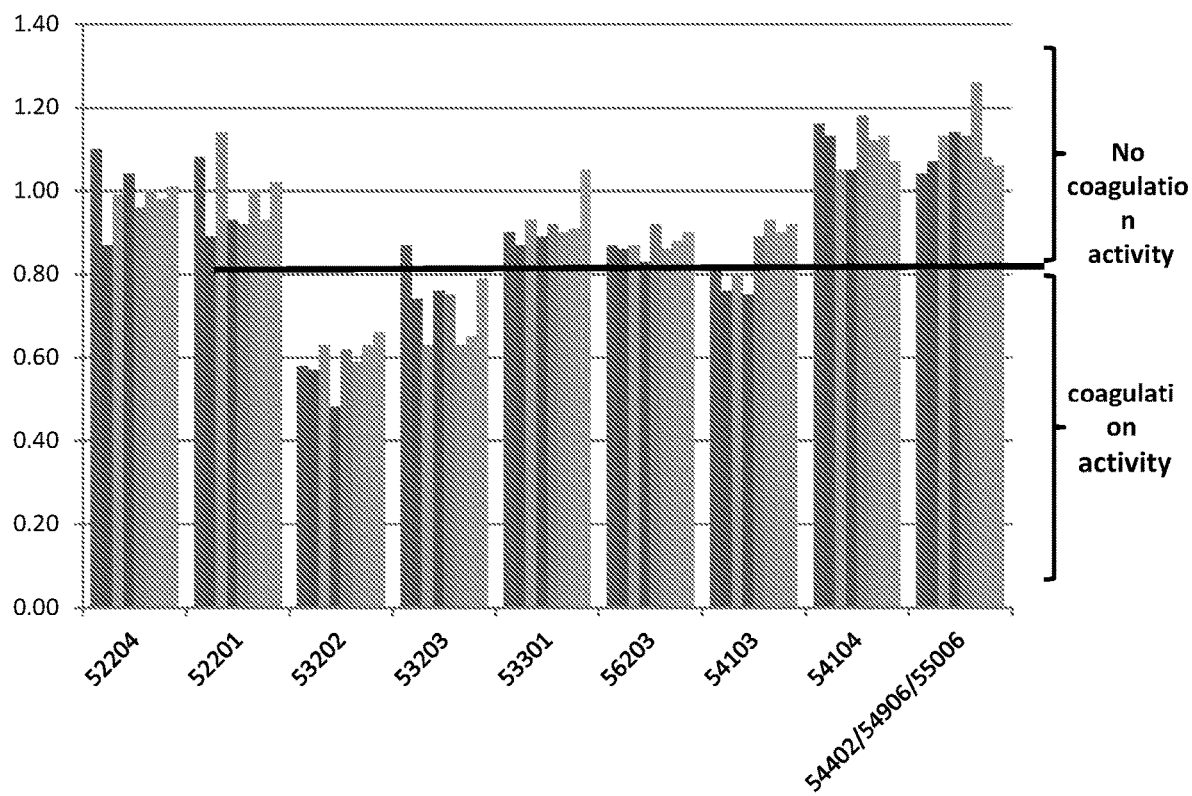
FIG. 1 depicts the Coagulation Activity of Anti-Rabies IPC Samples.

IPC samples from eight Anti-D lots were used to determine coagulation activity by the NAPTT method as described in the description of FIG. 1.

Figure 3:
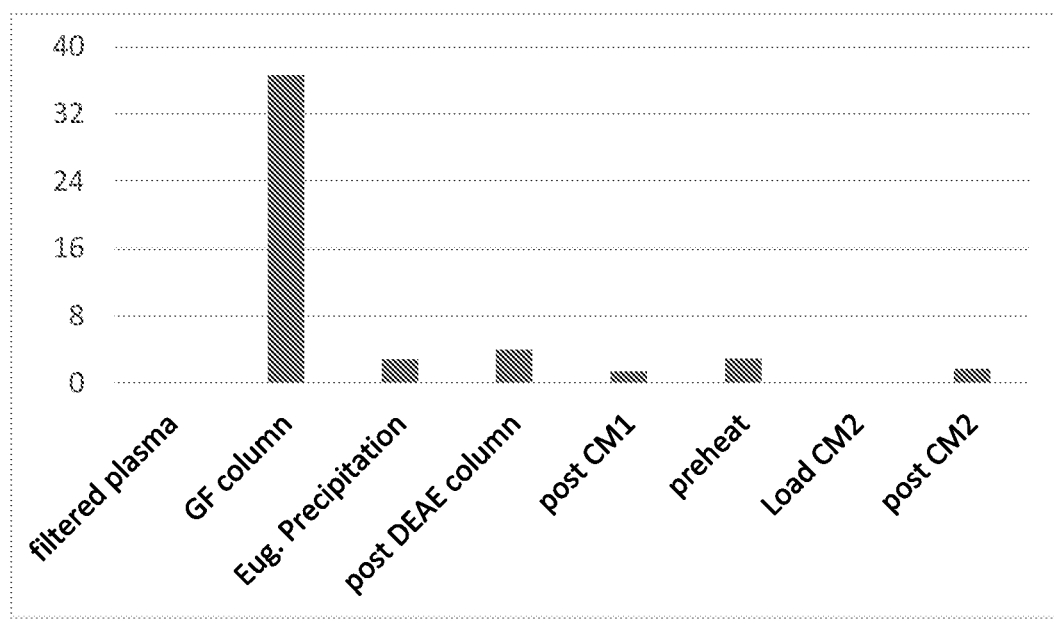

FIG. 3 demonstrates FXIa activity of Anti-Rabies IPC Samples (mIU/ml).

IPC samples from Anti-Rabies batch were used to determine FXIa activity by a kit from Hyphen LTD. IPC samples were taken from eight manufacturing steps throughout the process: filtered plasma pool (52201), post Gel Filtration—GF (53202), post Euglobulins precipitation (53203), post DEAE column (53301), post CM1 (56203), preheat sample, Load CM2 (54103), post CM2 (54104). The assay measures activity of FXa by a specific chromogenic substrate. Since FXa is activated by FXIa, the results of FXa activity are directly related to FXIa levels.

Figure 4:
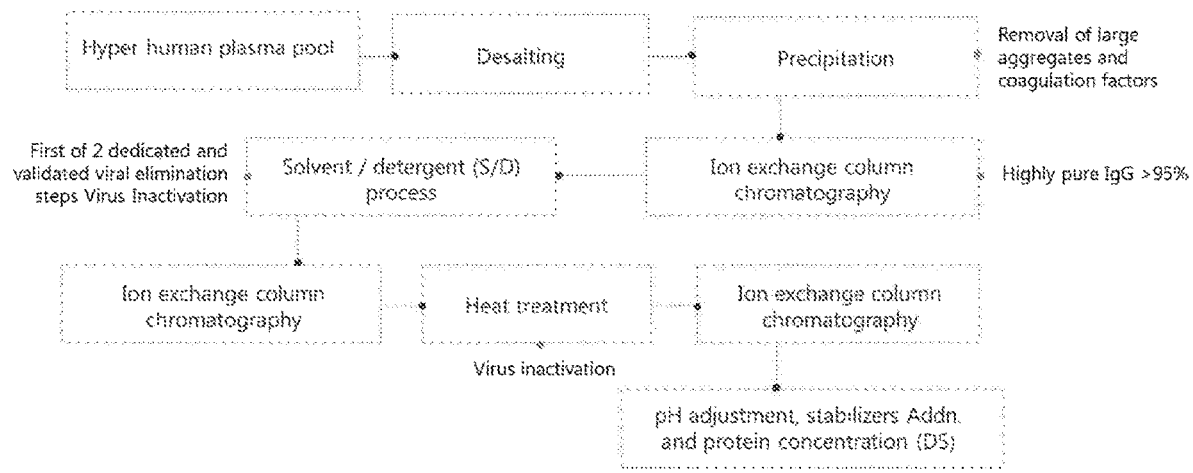

FIG. 4 demonstrates the manufacture flow chart of the immunoglobulin composition of the present invention.

DETAILED DESCRIPTION OF THE INVENTION

The invention relates to a method for removing thrombogenic agents from an immunoglobulin preparation and to the immunoglobulin composition produced by said method.

The composition comprises polyclonal immunoglobulin, which is typically obtained from plasma of human donors. Preferably, the plasma from multiple donors is pooled. Normal human IgG can be obtained with a purity of at least 95% IgG. Thus, in one embodiment, the IgG contained in the composition used in the method according to the invention generally has a purity of at least 95% IgG, preferably at least 96% IgG, more preferably at least 98% IgG, even more preferably at least 99% IgG. Preferably it contains only minor amounts of IgA.

The improved process of the present invention offers high productivity, lower production costs and easier implementation in comparison with the processes in the prior art.

Definitions

It must be noted that, as used in the subject specification, the singular forms "a", "an" and "the" include plural aspects unless the context clearly dictates otherwise.

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

In the absence of any indication to the contrary, reference made to"%" content throughout this specification is to be taken as meaning % w/w (weight/weight).

As used herein, the term "about" denotes an approximate range of plus or minus 10% from a specified value. For instance, the language "about 20%" encompasses a range of 18-22%. As used herein, about also includes the exact amount. Hence "about 20%" means "about 20%" and also "20%".

In the present context the term "fraction" relates to a portion of the protein solution, which may be separated from the supernatant by a fractionation process, such as filtration, microfiltration, centrifugation, distillation or chromatography and the fraction may be either a combination of compounds or a pure compound. In an embodiment of the present invention the fraction may be in the form of a liquid (a liquid fraction), a sediment (a sediment fraction) or a precipitate (a precipitated fraction).

In the present context the term "column" relates to any kind of container which can be supplied with at least one inlet and at least one outlet for the application of the protein solution to the column and subsequent to elute the protein.

"Affinity chromatography" is generally based on a highly specific biological interaction such as that between antigen and antibody, enzyme and substrate, or receptor and ligand.

Chromatography can be performed using any means known to persons skilled in the art. For example, the chromatography steps can use axial flow columns, such as those available from GE Healthcare, Pall Corporation and Bio-Rad, or radial flow columns, such as those available from Proxcys. The chromatography steps can also be conducted using expanded bed technologies.

As used herein, the term "ultrafiltration (UF)" encompasses a variety of membrane filtration methods in which hydrostatic pressure forces a liquid against a semi-permeable membrane. Suspended solids and solutes of high molecular weight are retained, while water and low molecular weight solutes pass through the membrane. This separation process is often used for purifying and concentrating macromolecular solutions, especially protein solutions. A number of ultrafiltration membranes are available depending on the size of the molecules they retain. Ultrafiltration is typically characterized by a membrane pore size between 1 and 1000 kDa and operating pressures between 0.01 and 10 bar, and is particularly useful for separating proteins from small molecules like sugars and salts.

As used herein, the term "diafiltration" is performed with the same membranes as ultrafiltration and can be run as either tangential flow filtration or dead-end filtration mode. During diafiltration, buffer is introduced into the recycle tank while filtrate is removed from the unit operation. In processes where the product is in the retentate (for example, IgG immunoglobulins), diafiltration washes components out of the product pool into the filtrate, thereby exchanging buffers and reducing the concentration of undesirable species.

The term "positively charged groups" as used herein refers to a molecule comprising chemical groups which carry a positive charge such as ammonium, alkyl ammonium, dialkylammonium, trialkyl ammonium, quaternary ammonium [e.g. diethylaminoethyl (DEAE), a dimethylaminoethyl or a trimethylaminoethyl], alkyl groups, amino functional group, and combination thereof.

The term "negative chromatography" refers to chosen conditions so that only a relatively small proportion (e.g. less than 25%) or none of a purified protein (i.e. immunoglobulin) binds to the chromatography support and it thus passes through the support in the chromatographic separation. The predominant portion of the therapeutic protein is thus present in the flow through material.

The term "positive chromatography" refers to chosen conditions so that the majority of a purified protein (i.e. immunoglobulin) binds to the chromatography support and therefore a step of elution the protein under non isocratic conditions is required to recover the protein.

The term "aggregates" refers to a chunk of protein material which contains high molecular weight oligomers. The molecular aggregates can be measured by HPLC.

The term "thrombogenic agent" refers to an agent that has the potential to induce fibrin clot formation. The term "thrombogenic agent" is used herein interchangeably with the terms hemostatic, thrombotic and pro-coagulant agent. Thrombogenic agent may be, for example, kallikrein, FXI, FXIa, Factor XII, thrombin and PKA. The term "thrombogenic agent" includes thrombogenic induced agents and "thrombosis-generating agents" such as agents that activate thrombogenic factors in the coagulation cascade.

As used herein, a "coagulation factor" refers to a protein involved in the intrinsic (contact activation) or extrinsic (tissue factor) pathway of the coagulation cascade. Non-limiting examples of coagulation proteins include, Factor II (prothrombin), Factor III (platelet tissue factor), Factor V, Factor VII, Factor VIII, Factor IX, Factor X, Factor XI, Factor XII, Factor XIII, von Willebrand Factor (vWF), and the like.

As used herein, the term "solvent" encompasses any liquid substance capable of dissolving or dispersing one or more other substances. A solvent may be inorganic in nature, such as water, or it may be an organic liquid, such as ethanol, acetone, methyl acetate, ethyl acetate, hexane, petrol ether, etc. As used in the term "solvent detergent treatment," solvent denotes an organic solvent (e.g., tri-N-butyl phosphate), which is part of the solvent detergent mixture used to inactivate lipid-enveloped viruses in solution.

The term "viral inactivation" refers both to the situation wherein viruses are maintained in the solution but are rendered non-viable (for example, by dissolving their lipid coat), and/or as to the situation wherein viruses are physically removed from the solution (for example, by size exclusion techniques).

As used herein, an "antibody" refers to a polypeptide substantially encoded by an immunoglobulin gene or immunoglobulin genes, or fragments thereof, which specifically bind and recognize an analyte (antigen). The recognized immunoglobulin genes include the kappa, lambda, alpha, gamma, delta, epsilon and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD, and IgE, respectively.

An exemplary immunoglobulin (antibody) structural unit is composed of two pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain (VL) and variable heavy chain (VH) refer to these light and heavy chains respectively. In a particular exemplary embodiment, the immunoglobulin will consist of an immunoglobulin preparation isolated from pooled plasma (preferably human plasma) comprising IgG immunoglobulins.

Immunoglobulins can be prepared from the plasma of unselected normal donors, while hyperimmunoglobulins can be prepared from the plasma of donors with high antibody titers against specific antigens. These hyperimmune donors may be identified during convalescent periods after infection or transfusion, or they may be specifically immunized to produce the desired antibodies.

As used herein, the term "enriched composition" refers to a protein composition isolated from a plasma sample, in which the purity of the protein is higher than the purity of the protein in the starting plasma sample. In one embodiment, a protein in an enriched composition is at least 25% more pure than in the starting plasma sample. In other embodiments, an enriched composition is at least 50%, 75%, 100%, 2-fold, 3-fold, 4-fold, 5-fold, 6-fold, 7-fold, 8-fold, 9-fold, 10-fold, or more pure than the starting plasma sample. For example, an enriched IgG composition in which 70% of the total protein is IgG is 7-fold enriched as compared to a starting plasma sample in which 10% of the total protein is IgG.

As used herein, the term "activity" refers to a functional activity or activities of a polypeptide or portion thereof associated with a full-length (complete) protein. Functional activities include, but are not limited to, biological activity, catalytic or enzymatic activity, antigenicity (i.e., the ability to bind or compete with a polypeptide for binding to an anti-polypeptide antibody), immunogenicity, ability to form multimers, and the ability to specifically bind to a receptor or ligand for the polypeptide.

As used herein, the term "Intravenous IgG" or "IVIG" refers generally to a therapeutic method of intravenously, subcutaneously, or intramuscularly administering a composition of IgG immunoglobulins to a patient for treating a number of conditions such as immune deficiencies, inflammatory diseases, and autoimmune diseases.

The IgG immunoglobulins are typically pooled and prepared from plasma. Whole antibodies or fragments can be used. IgG immunoglobulins can be formulated in higher concentrations (e.g., greater than 10%) for subcutaneous administration, or formulated for intramuscular administration. This is particularly common for specialty IgG preparations which are prepared with higher than average titers for specific antigens (e.g., Rho D factor, rabies, etc.).

The term "detectable" refers, for example, to a level detected using a method of analysis as described below in the Materials and Methods section.

The term "subject" includes animals of mammalian origin, including humans. In one embodiment, the subject is a patient.

As used herein, the term "protein" is intended to include any recombinant or purified polypeptide including, but not limited to, a naturally-occurring, modified, or synthesized polypeptide, and multimers, fragments (e.g., a biologically active fragment), or variants thereof.

As used herein, the term "plasma product" refers to a protein that can be generally characterized as a component of blood or blood fraction of a human or a non-human.

By "isolated" is meant present in an environment removed from a natural state or otherwise subjected to human manipulation. Isolated material may be substantially or essentially free from components that normally accompany it in its natural state, or may be manipulated so as to be in an artificial state together with components that normally accompany it in its natural state.

By "purified" is meant enriched, concentrated or otherwise having a specific activity, amount or concentration greater than in an initial state or form.

The term "pharmaceutical composition" is intended to be used herein in its broader sense to include preparations containing the composition according to the present invention e.g. antibodies, used for therapeutic purposes. The pharmaceutical composition intended for therapeutic use should contain a therapeutic amount of a composition according to the present invention. Pharmaceutical compositions for use in accordance with the present invention may be formulated in conventional manner using one or more physiologically acceptable carriers, which facilitate processing of the active compounds into preparations which can be used pharmaceutically. Proper formulation is dependent upon the route of administration chosen.

As used herein, the term "therapeutically effective amount or dose" or "sufficient/effective amount or dose," refers to a dose that produces effects for which it is administered. The exact dose will depend on the purpose of the treatment, and will be ascertainable by one skilled in the art using known techniques (see, e.g., Lieberman, Pharmaceutical Dosage Forms (vols. 1-3, 1992); Lloyd, The Art, Science and Technology of Pharmaceutical Compounding (1999); Pickar, Dosage Calculations (1999); and Remington: The Science and Practice of Pharmacy, 20th Edition, 2003, Gennaro, Ed., Lippincott, Williams & Wilkins; the disclosures of which are herein incorporated by reference in their entireties for all purposes).

The terms "treating" or "treatment" as used herein refers to taking steps to obtain beneficial or desired results, including clinical results. Beneficial or desired clinical results include, but are not limited to, alleviation or amelioration of one or more symptoms associated with a disease, delay or slowing of that disease, amelioration, palliation or stabilization of that disease, and other beneficial results.

The term "prophylactic treatment" refers to taking steps to prevent the disease, and in particular infectious disease.

The terms "dose" and "dosage" are used interchangeably herein. A dose refers to the amount of active ingredient given to an individual at each administration. The dose will vary depending on a number of factors, including frequency of administration; size and tolerance of the individual; severity of the condition; risk of side effects; and the route of administration. One of skill in the art will recognize that the dose can be modified depending on the above factors or based on therapeutic progress. The term "dosage form" refers to the particular format of the pharmaceutical, and depends on the route of administration. For example, a dosage form can be in a liquid, e.g., a saline solution for injection.

The term "passive immunization" or "passive vaccination" is used herein interchangeably and refers to a process of providing or administering an exogenous antibody or a fragment thereof to an organism in order to treat an infectious disease caused by a pathogen or to prevent a contagion by that pathogen.

According to one embodiment, the composition produced by the process of the present invention is formulated in the form selected from the group consisting of aqueous solution and a powder. According to another embodiment, the pharmaceutical composition is devoid of a stabilizer.

For injection, the composition of the invention may be formulated in aqueous solutions, preferably in physiologically compatible buffers such as Hank's solution, Ringer's solution, or physiological saline buffer.

According to some embodiments, the composition produced by the process of the present invention is stable for at least 12 months, preferably for at least 24 months, more preferably for at least 30 months. Each possibility represents a separate embodiment of the present invention.

As used herein, the term "stabilizing agent" refers to a compound that stabilizes the active ingredient within the pharmaceutical preparation. "Stabilization" refers to the process of preventing the loss of specific activity and/or changes in secondary structure from the native glycoproteins. Typically, such stabilizers include albumin, amino acids, sucrose and mannitol.

As used herein, the term "medical condition" includes, but is not limited to, e.g, any condition or disease manifested as one or more physical and/or psychological symptoms for which treatment and/or prevention is desirable, and includes previously and newly identified diseases and other disorders. For example, a medical condition may be a rabies infection.

As used herein, the term "rabies" refers to viruses of the Lyssavirus genus, in the family Rhabdoviridae, order Mononegavirales. Lyssaviruses have helical symmetry, with a length of about 180 nm and a cross-sectional diameter of about 75 nm. These viruses are enveloped and have a single stranded RNA genome with negative-sense. The genetic information is packaged as a ribonucleoprotein complex in which RNA is tightly bound by the viral nucleoprotein. The RNA genome of the virus encodes five genes whose order is highly conserved: nucleoprotein (N), phosphoprotein (P), matrix protein (M), glycoprotein (G) and the viral RNA polymerase (L).

Anti-D Antibodies

The development of anti-D antibodies generally results from feto-maternal haemorrhage (FMH) occurring in rhesus D (RhD)-negative women who carry an RhD-positive fetus. In later pregnancies, anti-D antibodies can cross the placenta, causing worsening rhesus haemolytic disease with each successive rhesus-positive pregnancy.

All RhD-negative pregnant women who do not have immune anti-D, should be offered additional routine prophylaxis with anti-D immunoglobulin (anti-D Ig) during the third trimester of pregnancy and after delivery.

The following examples are presented in order to more fully illustrate some embodiments of the invention. They should, in no way be construed, however, as limiting the broad scope of the invention. One skilled in the art can readily devise many variations and modifications of the principles disclosed herein without departing from the scope of the invention.

Example 1: Preparation and Evaluation of the Immunoglobulin Composition

Material and Methods

NAPTT

In order to evaluate the coagulation activity of the IgG compositions in different stages of the manufacturing process, an assay was developed based on the Ph. Eur. assay of activated coagulation factors. The assay relies on the non-activated partial thromboplastin time (NAPTT) coagulation screening test, which involves the re-calcification of plasma in the presence of a standardized amount of the phospholipid Cephalin (platelet substitute). The NAPTT test measures the activated coagulation factors of the intrinsic pathways XII, XI, IX, VIII, X, V, II (Prothrombin) and I (Fibrinogen) in platelet-poor plasma.

As a control, the coagulation time of a blank sample (buffer) was also tested. The ratio between the coagulation time of the tested sample and the blank sample is the value representing the sample thrombogenicity and is termed Relative Coagulation Time (RCT). A sample that coagulates within <80% of blank sample coagulation time (RCT<0.8) was considered thrombogenic.

IPC samples from eight Anti-Rabies lots (FIG. 1, FIG. 3) and from eight Anti-D lots (FIG. 2) were used to determine coagulation activity by the NAPTT method. IPC samples were taken from nine manufacturing steps throughout the process: post plasma pool (#52204), filtered plasma pool (#52201), post Gel Filtration—GF (#53202), post Euglobulins precipitation (#53203), post DEAE column (#53301), post CM1 (#56203), Load CM2 (#54103), post CM2 (54104) and Drug substance—DS (#54402/#54906/#55006).

NAPTT Clotting Assay:

The APTT C.K. Prest reagent bottle (Stago, cat No. 00847) and the $CaCl_2$ solution bottle (Stago, cat No. 00367) were warmed to room temperature and 37° C. (respectively). Then, four barrettes were placed in the appropriate pre-warm slots of the coagulometer (Start 4, Stago) incubation area and one metal ball was added to each well.

Pool Norm solution (Stago, cat No. 00539) was added, followed by 50 µl of C.K. Prest at an optimal dilution, where the blank result was found to be between 200 and 350 seconds.

50 µl of the proper sample or blank were added to each well according to Table 1. The measurement was done according to the coagulometer Manual.

Briefly, an incubation of 300 seconds was followed by transferring the barrette to the slots of the measurement area and counting by pressing the instrument timer button followed by an immediate addition of 50 µl CaCl2 to each well using the wire connected stepper.

The coagulometer stops the counting just after the coagulation event in each well. Automatic printing of the results occurs when plasma coagulation has been completed in all 4 wells of the barrette or after 500 seconds.

TABLE 1

Layout design for
samples and blanks
in the barrette

BL
Sample 1
BL
Sample 2

BL-Blank, Tris Buffer Solution instead of sample.

Measurement:

The test was repeated three times for each sample tested. For each barrette, the average of the Blanks coagulation time was determined and the ratio between each sample coagulation time and its Blanks average coagulation time was calculated (relative coagulation time-RCT).

Factor XIa (FXIa) Activity

The FXIa activity of the IgG compositions in different stages of the manufacturing process was tested by an assay that was developed based on a commercial kit from Hyphen.

The assay uses platelets-poor plasma, in the presence of Phospholipids (PLPs), calcium and thrombin, activated FXI (FXIa), present in the tested sample is able to activate Factor IX into FIXa, that forms an enzymatic complex with cofactor, Factor VIII:C. This complex activates Factor X into Factor Xa, which its generated amount is directly related to the amount of Factor XIa to be measured. Generated Factor Xa is then measured by its specific activity on a Factor Xa chromogenic substrate.

Each sample was tested in duplicate and the reported result was the average of these two tests.

IPC samples from seven Anti-R lots were used to determine coagulation activity by the FXIa assay. IPC samples were taken from nine manufacturing steps throughout the process: post plasma pool (#52204), filtered plasma pool (#52201), post Gel Filtration—GF (#53202), post Euglobulins precipitation (#53203), post DEAE column (#53301), post CM1 (#56203), Load CM2 (#54103), post CM2 (54104) and Drug substance—DS (#54402/#54906/#55006).

The Process for Removing the Active Coagulation Factors Content of the Immunoglobulin Composition Gel filtration step that induces activation and aggregation of coagulation factors was developed. The following step is a unique precipitation step, based on low pH and low conductivity that leads to precipitation of large complexes including activated coagulation factors and aggregates, while leaving the intact IgG molecules in the solution. Remaining non-desirable contaminants and activated coagulation factors are removed by using a weak Anion exchange column where the IgG molecules are passing in the flow-through of the column, while residual contaminants aggregates and active coagulation factors remain on the column.

This combination allows significant reduction in thrombogenic activity and aggregates at the final drug product as demonstrated using NAPTT coagulation assays (FIGS. 1-2) and by testing of FXIa activity (FIG. 3) at these steps of IgG purification process.

Gel Filtration Step:

The filtered plasma is passed on a Sephadex G-25 resin for gel filtration chromatography. Acetate buffer (5 mM) was chosen to fit with the subsequent step of euglobulin precipitation that requires low pH (4.9). Flow rate of 100 cm/hr. the maximal load volume is 0.225 column volume (CV) in order to obtain low conductivity in the pooled plasma solution—as a preparation for the euglobulin precipitation step. Temperature is kept at 18-25° C.

Euglobulin Precipitation Step:

The product from the previous step is in the pH range of about 6-8 and conductivity range of about 1-2 mS/cm. For efficient precipitation of aggregates and complexes of activated coagulation factor the pH is adjusted to 4.9 and the conductivity to 0.9-1.0 mS/cm. Precipitation is for 8 to 72 hrs at 18-25° C.

Ranges: pH 4.6-5.2, conductivity 0.75-1.2 mS/cm, Temp 17-25° C.

Weak Anion Exchange DEAE Column:

The conditions that are used during loading and wash of the column allow passing of the IgG fraction, while the non-desirable contaminants including remaining active coagulation factors and aggregates remain in the column. This step lead to a high >95% purified IgG fraction with low coagulation activity and low aggregates level.

Following precipitation the supernatant is filtered and the pH and conductivity are adjusted to 8.2 and 2.9 mS/cm, respectively. The solution is loaded on the DEAE column and the column is washed with the equilibration buffer (50 mM Tris acetate in 15 mM NaCl at pH 8.0-8.4, and conductivity of 2.75-3.05 mS/cm). The IgG fraction is collected during the loading and the wash steps.

Ranges: pH 7.9-8.5 and conductivity of 2.65-3.15 is still acceptable.

The characterizations of the immunoglobulin composition of the present invention are presented in Table 2. The manufacturing parameters and analytical test results of IPC samples from Anti-R lot RA5131115 are presented in Table 3.

TABLE 2

Characterizations of the immunoglobulin composition

| attribute | values |
|---|---|
| FXIa activity | <8 mIU/ml |
| RCT (NAPTT) | ≥0.8 |
| Aggregates level | ≤3% |

TABLE 3

Manufacturing parameters and analytical test results of Anti-R lot RA5131115 composed from batches 080915AR and 090915AR

| Parameter | RA5131115 | 080915AR | 090915AR |
|---|---|---|---|
| GF -load volume per loading cycle (total of eight loading cycles) (L) | — | 37 (in 7 cycles) and 40 (in 1 cycles) | 37 (in 5 cycles) and 38 (in 3 cycles) |
| GF -column pressure (bar) | — | 0.1-0.2 | 0.1-0.4 |
| GF - flow rate (L/min) | — | 9.2 | 9.2 |
| Euglobulin precipitation - pH | — | 5 | 5 |
| Euglobulin precipitation - conductivity (mS/cm) | — | 0.95 | 0.95 |
| Euglobulin precipitation - temperature (° C.) | — | 24 | 24 |
| Euglobulin precipitation - incubation time (hr) | — | 12 | 12 |
| DEAE - pH of load | — | 8.1 | 8.1 |
| DEAE - conductivity of load (mS/cm) | — | 2.9 | 2.7 |
| DEAE - column load per loading cycle (total of five loading cycles) (L) | — | 166 (in all 5 cycles) | 162 (in 3 cycles) and 163 (in 1 cycle) and 164 (in 1 cycle) |
| DEAE - flow rate (L/min) | — | 16.6 | 16.6 |
| DEAE - column pressure towards the end of loading (bar) | — | 14 | 13-15 |
| Aggregates in DP at release (%) | 0.2 | — | — |
| Monomers and dimers at release (%) | 99.8 | — | — |
| Aggregates in DP after 12 month (%) | 0.5 | — | — |
| Monomers and dimers after 12 month (%) | 99.5 | — | — |
| NAPTT (RCT) | 1.11 | — | — |
| FXIa (mIU/ml) | 2.35 | — | — |

Example 2: Rabies Clinical Study of the Safety and Effectiveness of Simulated Post-Exposure Prophylaxis with the Anti-Rabies Human Immune Globulin of the Present Invention with Co-Administration of Active Vaccine in Healthy Subjects Methods The study was designed to evaluate the safety and efficacy (i.e., generation of antibody level) of the Anti-Rabies Human Immune Globulin produced by the method of the present invention (HRIG) by comparison to another US FDA registered and commercially available (HyperRAB). Since classical efficacy studies of HRIG in rabies patients are both impossible and unethical, efficacy in this study was defined as the ability of the HRIG product, when co-administered with active rabies vaccine, to produce circulating anti-rabies antibodies in expected quantities at various time points up to 14 days after an IM injection.

The HRIG drug product of the present invention is a sterile solution of anti-rabies immunoglobulin for intramuscular (IM) administration. It is prepared from the plasma of rabies-immune individuals in full compliance with the applicable requirements of plasma-derived product safety. It has a labeled potency of 150 IU/ml, and contains 0.3M glycine as a stabilizing agent. The HRIG is calibrated in International Units (IU), by comparison with the Standard Rabies Immune Globulin Reference Serum (US Food and Drug Administration [FDA]/Center for Biologics Evaluation and Research [CBER]).

The HRIG is prepared from the plasma of healthy donors who have been immunized with rabies vaccine and have developed high titers of anti-Rabies antibody in their serum (hyperimmune plasma). The plasma is processed and purified using the method of the present invention. To reduce the risk of blood-borne viral transmissible diseases, each unit of donor plasma is tested for Hepatitis B Surface Antigen (HBsAg), antibodies to HIV types 1 and 2 (anti HIV-1/2), antibodies to HCV (anti HCV) and Serological Testing for Syphilis. Because viremia precedes serum conversion by several days to weeks, Nucleic Acid Amplification Technology (NAT) testing is performed to cover the infectious window period for detection of HIV, HBV, HAV and HCV in source plasma pools. The tests are performed either on each donation individually and/or on mini-pools which enables traceability of a positive result to the individual plasma unit. After the plasma units are pooled, the manufacturing pool is screened and must be non-reactive to HBsAg, anti HCV and anti HIV-1/2, negative to HCV by NAT and the level of parvovirus B19 by NAT should be not more than $10^4$ IU/ml.

In order to further reduce the risk of viral transmission during the manufacturing process, three specific viral inactivation/removal steps are employed: (1) Treatment with Solvent Detergent (S/D) for inactivation of lipid-enveloped viruses, (2) Heat Treatment for inactivation by denaturation of heat-labile viruses (58-61° C. for NLT 9.5 h) and (3) Nanofiltration using Planova 20N filters for the removal of both lipid-enveloped and non-enveloped viruses.

The HRIGs were given IM on Day 0, with co-administration of a rabies vaccine (RabAvert rabies vaccine), given on Days 0, 3, 7, 14, and 28. The primary endpoint was the proportion of subjects with an IgG antibody titer ≥0.5 IU/mL on Day 14, a threshold based on the WHO-recommended minimum anti-rabies titer threshold value (0.5 IU/mL) for conferring protection during rabies exposure.

Enrollment and Demographics

A total of 118 subjects were randomized and treated with the HRIG of the present invention (59 subjects) or HRIG Comparator (59 subjects). Demographic characteristics were comparable between treatment groups, with the majority of subjects being female (63.6%), White (93.2%), not of Hispanic or Latino ethnicity (97.5%), and a median age of 47.5 years old.

Efficacy:

The primary analysis was conducted on the As-Treated Population. Most subjects in the HRIG group (55 of 56 subjects; 98.2%) and all subjects in the Comparator group had an anti-rabies IgG antibody titer ≥0.5 IU/mL on Day 14. The difference between the proportion of subjects with an anti-rabies IgG antibody titer ≥0.5 IU/mL on Day 14 in the HRIG and Comparator groups was −1.8% (90% CI: −8.2, 3.1). The lower limit of the 90% CI was greater than the pre-specified non-inferiority margin of −10%, thus demonstrating that HRIG was non-inferior to HRIG Comparator for the primary endpoint (Table 4).

TABLE 4

Subjects with Geometric Mean Anti-Rabies IgG Antibody Titer ≥0.5 IU/mL on Day 14 - Primary Endpoint (As-Treated Population)

|  | HRIG + Vaccine (N = 57) | Comparator + Vaccine (N = 58) |
|---|---|---|
| Number of subjects who had IgG antibody titer values, n | 56 | 58 |
| IgG antibody titer ≥0.5 IU/mL, n (%) | 55 (98.2) | 58 (100) |
| Exact 95% CI for proportion | (90.4, 100) | (93.8, 100) |
| Difference (Pa-Pb)a (%) | −1.8 | |
| Exact 90% CI for difference b | (−8.2, 3.1) | |

Abbreviations: CI = confidence interval; HRIG = Human Rabies Immune Globulin; IgG = immunoglobulin G; RFFIT = Rapid Fluorescent Focus Inhibition Test; SAP = Statistical Analysis Plan Notes: The RFFIT test was used to evaluate the primary endpoint presented in this table, as specified in the protocol.
a 'Pa' and 'Pb' are the proportion of participants with IgG antibody titer ≥0.5 IU/mL on Day 14 in HRIG and Comparator groups, respectively.
b This exact 90% CI for the difference is based on Farrington-Manning score statistic.

Thus HRIG of the present invention was shown to be non-inferior to the Comparator for the primary efficacy endpoint of the proportion of subjects with an anti-rabies IgG antibody titer ≥0.5 IU/mL on Day 14.

Example 3: Comparison of Impurities in Three HRIG Products

Human Anti-Rabies Immuno-globulin (HRIG) products contain impurities originating from the donors' plasma or the process. These may include activated coagulation factors, such as FXIa; IgA, which may elicit undesirable immune response in IgA deficient patients, and IgG aggregates, which may be involved in anti-drug-antibodies formation and Immunogenicity, and have been considered a reason for adverse reactions associated with Intravenous Immunoglobulin (IVIG).

Human Anti-Rabies Immuno-globulin (HRIG) products (HRIG of the present invention; and other US FDA registered and commercially available HRIG) were compared for the presence of activated coagulation factor XI (FXIa), for content of Immuno-globulin A (IgA) and IgG aggregates.

Methods:

The percentage of IgG aggregates was determined by SEC-HPLC. IgA content was established by a Quantitative nephelometry test (Minineph, The Binding Site). FXIa was tested using ROX FXIa Chromogenic Assay kit (Rossix AB, Mölndal, Sweden).

Results:

The HRIG of the present invention had a fundamentally lower content of FXIa (0.36, vs. >100 mIU/ml for others); undetectable IgA levels (<0.03 mg/ml, vs. 0.23 or higher for others) and IgG aggregate percentage of 0.6% vs. 1.6% for others.

The improved purity profile may be attributed to the unique production process which differs from the Cohn fractionation-based processes utilized by other manufacturers. Removal of impurities is paramount for the reduction of risks associated with the IgG preparation use, such as thromboembolic events, hypersensitivity reactions and immunogenicity.

Example 4: Evaluation of the Thrombogenic Activity of the IgG Compositions by Thrombin Generation Assay (TGA)

In order to evaluate the thrombogenic activity of the IgG compositions with another analytical method, a Thrombin Generation Assay (TGA) method was developed for testing the drug substance and drug product material. The method was developed and was validated by Haemtech Biopharma Services (HBS, USA) and was designed and performed on the Calibrated Automated Thrombogram (CAT) platform. The test method assessed relative amounts of process related impurities in the IgG test samples that may have thrombogenic activity. The assay was based on two observations: 1) FXIa is the main procoagulant impurity found in lots of IgG products that have been associated with thrombotic adverse events (TAE); 2) procoagulant IgG lots enhance thrombin generation in recalcified FXI deficient plasma. Thrombin generation in the test samples was measured with a fluorogenic thrombin substrate, and peak thrombin values (nM) were compared to a standard curve developed with human factor Xia (FXIa). Each sample was tested in triplicates and the comparison of the mean value from the triplicate tests to the standard curve generates the final result. The resultant FXIa-like activity was reported in mU/mL.

Since the TGA method was implemented for testing Drug Substance material, several Anti-R batches were tested and the results are present in Table 5. Overall, the results demonstrate low thrombogenic activity in the DS samples of up to 2.58 mU/mL

TABLE 5

TGA results of several Anti-R batches

| Lot No. | TGA result (mU/mL) |
| --- | --- |
| 220916AR | <0.23 |
| 230916AR | 0.56 |
| 010117AR | 0.31 |
| 030217AR | 0.38 |
| 060217AR | 0.29 |
| 070217ER | 0.37 |
| 080217ER | 0.42 |
| 090217ER | 0.6 |
| 070317BD | 1.33 |
| 110317AR | 0.3 |
| 130417AR | <0.23 |
| 170917AR | <0.23 |
| 210917AR | 2.58 |
| 250917AR | <0.23 |
| 230917AR | 0.29 |
| 010118AR | <0.23 |
| 030118AR | <0.23 |
| 040118AR | 0.68 |
| 070118AR | 0.34 |
| 090118AR | 1.55 |
| 100218AR | 0.37 |
| 130218AR | 2.48 |
| 140218AR | 1.09 |
| 120218AR | <0.23 |

*LOQ = 0.23 mU/mL

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

The invention claimed is:

1. A method of activating and removing a thrombogenic agent from an immunoglobulin containing solution, comprising subjecting human plasma or fractions thereof to gel filtration column chromatography, and an euglobulin precipitation step;
   wherein the euglobulin precipitation incubation time is about 8-72 hrs;
   wherein the immunoglobulin containing solution is kept at a temperature in the range of about 24° C. to about 25° C.; and
   wherein the method further comprises an anion exchange column chromatography enrichment step for enriching the immunoglobulin containing solution; and
   wherein the method results in an isolated or purified immunoglobulin composition comprising factor XI activity equal or below 8 mIU/ml.

2. The method according to claim 1, wherein the euglobulin precipitation is performed at a pH of about 4.6 to about 5.2.

3. The method according to claim 1, wherein the conductivity during the euglobulin precipitation step is about 0.9 to about 1.0 millisiemens (mS)/cm.

4. The method according to claim 1, wherein the anion exchange column is a diethylaminoethyl (DEAE) column.

5. The method according to claim 1, further comprising at least one repetition of a virus eliminating treatment.

6. The method according to claim 1, wherein the thrombogenic agent is a coagulation factor selected from the group consisting of Factor II, Factor V, Factor VII, Factor VIII, von Willebrand factor, Factor IX, Factor X and Factor XI.

7. A method of activating and removing a thrombogenic agent or IgG aggregates from an immunoglobulin containing solution, comprising:
   (a) subjecting human plasma or fractions thereof to gel filtration column chromatography;
   (b) subjecting the protein containing fraction obtained by step (a) to euglobulin precipitation; and
   (c) loading the supernatants obtained by step (b) on an anion exchange column;
   wherein the euglobulin precipitation incubation time is about 8-72 hrs;
   wherein the immunoglobulin containing solution is kept at a temperature in the range of about 24° C. to about 25° C.; and
   wherein the method results in an isolated or purified immunoglobulin composition comprising factor XI activity equal or below 8 mIU/ml.

8. The method according to claim 7, wherein the euglobulin precipitation is performed at a pH of about 4.6 to about 5.2.

9. The method according to claim 7, wherein the conductivity during the euglobulin precipitation step is about 0.9 to about 1.0 mS/cm.

10. The method according to claim 7, wherein the anion exchange column is a diethylaminoethyl (DEAE) column.

11. The method according to claim 7, further comprising at least one repetition of a virus eliminating treatment.

12. The method according to claim 7, wherein the thrombogenic agent is a coagulation factor selected from the group consisting of Factor II, Factor V, Factor VII, Factor VIII, von Willebrand factor, Factor IX, Factor X and Factor XI.

* * * * *